United States Patent [19]
Haake

[11] Patent Number: 5,824,321
[45] Date of Patent: Oct. 20, 1998

[54] CLONED LEPTOSPIRA OUTER MEMBRANE PROTEIN

[75] Inventor: David A. Haake, Culver City, Calif.

[73] Assignee: The Regents of the University of California, Oakland, Calif.

[21] Appl. No.: 886,863

[22] Filed: Jul. 1, 1997

Related U.S. Application Data

[62] Division of Ser. No. 249,013, May 25, 1994, Pat. No. 5,643,754.

[51] Int. Cl.⁶ .................................................. A61K 39/002
[52] U.S. Cl. ........................ 424/266.1; 530/350; 530/820; 530/822; 424/265.1
[58] Field of Search ..................................... 530/350, 403, 530/820, 822; 435/69.3, 69.7, 71.1, 172.1; 424/265.1, 266.1, 269.1

[56] References Cited

U.S. PATENT DOCUMENTS 5,679,353  10/1997  Hall et al. .............................. 424/269.1

OTHER PUBLICATIONS

Dunn et al., "Outer Surface Protein A (OspA) from the Lyme Disease Spirochete, *Borrelia burgdorferi:* High Level Expression and Purification of a Soluble Recombinant Form of OspA," *Protein Expression and Purification,* vol. 1, No. 2, (2pgs.).

Kida et al., "Immunological and Morphological Analysis of Sodium Dodecyl Sulfate Extract of Leptospira," *Zbl. Bakt. HY6 I. ABT. Orig. A 236,* pp. 328–335 (1976).

Nicholson, Vivian and Prescott, John, "Outer Membrane proteins of three pathogenic Leptospira species," *Veterinary Microbiology,* 36, pp. 123–138 (1993).

Zuerner et al., "Characterization of outer member and secreted proteins of Leptospira interrogans serovar pomona," *Microbial Pathogenesis,* 10:pp. 311–322, (1991).

Brown et al., "Protein and Antigen Profiles of Prevalent Serovars of Leptospira interrogans," *Infection and Immunity,* vol. 59, No. 5, pp. 1772–1777 (May, 1991).

Haake et al., "Molecular Cloning and Sequence Analaysis of the Gene Encoding OmpL 1, a Transmembrane Outer Membrane Protein of Pathogenic Leptospira spp.," *Journal of Bacteriology,* vol. 175, No. 13, pp. 4225–4234, (Jul., 1993).

Nunes–Edwards et al. "Identification and Characterization of the Protein Antigens of Leptospira interrogans serovar hardjo," *Infection and Immunity,* vol. 48, No. 2, pp. 492–497, (May, 1985).

*Primary Examiner*—Lorraine Spector
*Attorney, Agent, or Firm*—Fish & Richardson P.C.

[57] ABSTRACT

An antigenic preparation is provided which contains a 63 Kd outer membrane protein from *Leptospira* which can be used immunologically as a vaccine for leptospirosis caused by this organism. Also provided in the invention are polynucleotides encoding the protein and antibodies which bind the protein which are useful in the diagnosis of leptospirosis.

10 Claims, 5 Drawing Sheets

```
GATCTTCATT TCTTTCCGAA AATTAAGTAA GACTTTATTT GTAAGGAGAG TGTAGCGGGA        60

TTTTCTAAGG AATTTCGGT TTAAATCAAT CTGAC ATG ACC AAA CGT TCT AAA          113
                                     Met Thr Lys Arg Ser Lys
                                      1               5

TAC CTT TTC CTA TTT TTA TTT CTT TTC TTT GGA ATC CAA ACT GGA ATT        161
Tyr Leu Phe Leu Phe Leu Phe Leu Phe Phe Gly Ile Gln Thr Gly Ile
            10              15                  20

CAA GCA CAA CTT TGG ATT CCA CCG GGT AGA CAG TAT ATG CAT CCC ACA        209
Gln Ala Gln Leu Trp Ile Pro Pro Gly Arg Gln Tyr Met His Pro Thr
      ↑ 25              30                  35

GAG CCG TTT ACT TAT GAC CTT GGG ATC AAT AAA TAT CAG AAA GAT TAT        257
Glu Pro Phe Thr Tyr Asp Leu Gly Ile Asn Lys Tyr Gln Lys Asp Tyr
        40              45                  50

TAT CTC TAT GTG GCG CCT ACC GTC AAT TTG AAC TTC GGA GGC GAT TTC        305
Tyr Leu Tyr Val Ala Pro Thr Val Asn Leu Asn Phe Gly Gly Asp Phe
 55              60                  65                      70

GGA GCC TCT CTG ACT TTA CCT TTA AAT TTT TTG ATC TAC GAT ACG GAG        353
Gly Ala Ser Leu Thr Leu Pro Leu Asn Phe Leu Ile Tyr Asp Thr Glu
                75              80                      85

CCG AAA CAA GAA AAT TCT AGG ATC GGA AAG CTT AGG TCT TTC GAT TAC        401
Pro Lys Gln Glu Asn Ser Arg Ile Gly Lys Leu Arg Ser Phe Asp Tyr
                90                  95                  100

AAT GAC AAA AGC GAT TAT CTT AGA TTG ATC AAT AAT ATT TGG TTT GGC        449
Asn Asp Lys Ser Asp Tyr Leu Arg Leu Ile Asn Asn Ile Trp Phe Gly
            105                 110                 115

CAG TAT GGA AAA TAC ACT CCC GGA GAA ATT ACA TAT TCT GCA TCT TTA        497
Gln Tyr Gly Lys Tyr Thr Pro Gly Glu Ile Thr Tyr Ser Ala Ser Leu
        120             125                 130

GGA AAA CTA TTC GAT GGT TAT ATA GGT CAC GGA ACG ATC GTA AAC CGG        545
Gly Lys Leu Phe Asp Gly Tyr Ile Gly His Gly Thr Ile Val Asn Arg
135             140                 145                 150

TAC GTA AAC AAT CAA CGT TTG GAT GTG TAT AAC GTA GGT CTT CAA GCA        593
Tyr Val Asn Asn Gln Arg Leu Asp Val Tyr Asn Val Gly Leu Gln Ala
            155                 160                 165

GAT ATA AAC AGT GAC TTT GGA GGA GTG CAG GTA TTT TCT AAT TCG ATC        641
Asp Ile Asn Ser Asp Phe Gly Gly Val Gln Val Phe Ser Asn Ser Ile
            170             175                 180

TAT ACG AGA GAA GTC AGT TCA GCA AGG GTT TAT ATC CGG CCC TTT GCC        689
Tyr Thr Arg Glu Val Ser Ser Ala Arg Val Tyr Ile Arg Pro Phe Ala
        185                 190                 195

GTT GGA TAT AAA CTT TTT GAT ATT GTT ACC GGC CGG TCC AAA TTT TTG        737
Val Gly Tyr Lys Leu Phe Asp Ile Val Thr Gly Arg Ser Lys Phe Leu
        200             205                 210

ACG ATG ATG ACA ATC GCA CAA GGA AAC GTA GCA GAC GAG GCT GGA AGA        785
Thr Met Met Thr Ile Ala Gln Gly Asn Val Ala Asp Glu Ala Gly Arg
215             220                 225                 230
```

FIG.1A

```
AGA AAA GTT TAT GAA GAA GTA GGG GCG GAA GAA AAG GAA TCT TAT CGC      833
Arg Lys Val Tyr Glu Glu Val Gly Ala Glu Glu Lys Glu Ser Tyr Arg
            235             240             245

GCT TTG ATC GAG GAT CAG AAG ACG CAC CAC AAA AAA GAA GAG ATG ATT      881
Ala Leu Ile Glu Asp Gln Lys Thr His His Lys Lys Glu Glu Met Ile
            250             255             260

CCT GTG GAT AAG AAA CCG GAA AAA CCT CGA AAT TTA AAA GAA ATA TTT      929
Pro Val Asp Lys Lys Pro Glu Lys Pro Arg Asn Leu Lys Glu Ile Phe
            265             270             275

AAT CAA GAT AAT TGG GTT AAC CGG TTT GCA ATT GGT TAT ACG ACT GCG      977
Asn Gln Asp Asn Trp Val Asn Arg Phe Ala Ile Gly Tyr Thr Thr Ala
            280             285             290

TTT GAT ACC AAA GCC CCT TCG GAA CTT AAG TTT GAT ACG ACT GGA AAA     1025
Phe Asp Thr Lys Ala Pro Ser Glu Leu Lys Phe Asp Thr Thr Gly Lys
295             300             305             310

TTG AGA GTG GAT GAA AAC GAC AAT CCA CTC GTC AAG TCT ACG GAA AGA     1073
Leu Arg Val Asp Glu Asn Asp Asn Pro Leu Val Lys Ser Thr Glu Arg
            315             320             325

CTT TCG ATC ACT GGT TTC GAT TTC GAA TAT AAA TTA CTC AGT GCG AAA     1121
Leu Ser Ile Thr Gly Phe Asp Phe Glu Tyr Lys Leu Leu Ser Ala Lys
            330             335             340

TAT ATA GAA CTG ACT CCC TAT TAC GAC GTA AAT AAA ATC AAA CAG ATA     1169
Tyr Ile Glu Leu Thr Pro Tyr Tyr Asp Val Asn Lys Ile Lys Gln Ile
            345             350             355

GAA AAC GCA AAA GGT ACA CAT TAC GGA GCG ATT CTT CGA TTG GGT GGA     1217
Glu Asn Ala Lys Gly Thr His Tyr Gly Ala Ile Leu Arg Leu Gly Gly
            360             365             370

AAG GAC ATT TAT GTA CAA ATA AAA CCT GAA TAT AGA AAT ATG ACT GCA     1265
Lys Asp Ile Tyr Val Gln Ile Lys Pro Glu Tyr Arg Asn Met Thr Ala
375             380             385             390

ACG TAT ATT CCT ATG TAT TTT GAT AGT TTT TAC GAA TTG GAA AGG TTT     1313
Thr Tyr Ile Pro Met Tyr Phe Asp Ser Phe Tyr Glu Leu Glu Arg Phe
            395             400             405

CAG AGT AAT TTA CAA AGT CAT ATT CCG CAG ACT AAA TTA GAA GCC CCA     1361
Gln Ser Asn Leu Gln Ser His Ile Pro Gln Thr Lys Leu Glu Ala Pro
            410             415             420

AAA TTA GCC GAT CCG GAT GGA TCT AAG ATA AAA GGA CAT TTT ACA CCT     1409
Lys Leu Ala Asp Pro Asp Gly Ser Lys Ile Lys Gly His Phe Thr Pro
            425             430             435

GTA TTA TTC AAC TTT TAT AGA TTT GCG ATT GAA TCG AAT TAC GAG AAT     1457
Val Leu Phe Asn Phe Tyr Arg Phe Ala Ile Glu Ser Asn Tyr Glu Asn
            440             445             450

TAT TCC GGG CCG AAT AAC TCT AGA GTA TTT TTA GGA GTT TAT ATT CCG     1505
Tyr Ser Gly Pro Asn Asn Ser Arg Val Phe Leu Gly Val Tyr Ile Pro
455             460             465             470
```

FIG.1B

```
CTT GGA AGT ATG TTC CTA ATT AAT GGA TAT TAT ATG AAA AAA GCT TTT        1553
Leu Gly Ser Met Phe Leu Ile Asn Gly Tyr Tyr Met Lys Lys Ala Phe
                475                 480                 485

AAA TTA GAC GAT CGA TCT CAA GGG GCC TTA GAA TTG GCG ATC AAT TTG        1601
Lys Leu Asp Asp Arg Ser Gln Gly Ala Leu Glu Leu Ala Ile Asn Leu
                490                 495                 500

GGG CTT GTA ACA GTT AGG CTT CAG AAT ATA CGT AAA TGG GTT TAT GAT        1649
Gly Leu Val Thr Val Arg Leu Gln Asn Ile Arg Lys Trp Val Tyr Asp
                505                 510                 515

ACG GCT TCT AGT CAA TAC GAA GCC CAA GAC GAA CAG AAG ATA TTA TTT        1697
Thr Ala Ser Ser Gln Tyr Glu Ala Gln Asp Glu Gln Lys Ile Leu Phe
                520                 525                 530

TCC GGT GGT TTA TAT TTT TAAAAAGTA TTTTTCTTC AAGTCTTGCG                 1745
Ser Gly Gly Leu Tyr Phe  *
535                 540

AGTAAAAATG CAAAAGCTGT TTCTGTACGA AGAACTCGAT CGGAAAGATT TAATTTTTTG      1805

AAACCGAAAC GTTTCCAAAA ATCGATTTCG
```

```
           *  . . | . . :   :            *  *       . :  . | : :  . . : : . : | *
OmpL2   17 FTYDLGINK        101 TPGEITYSASLGKLFDGYIGHG----------TIVN-RYVN
TBP1    14 DTIQVKAKK         59 DPGIAVVEQG-RGASSGYSIRG--MDKNRVSLTVDGLAQI
BtuB     6 DTLVVTANR         49 LPGVDITQNGGSGQLSSIFIRG--TNASHVLVLIDGVRLN
Cir      6 ETMVVTASS         49 VPGVQLTNEG--DNRKGVSIRG--LDSSYTLILVDGKRVN
IutA     6 ETFVVSANR         52 IPGLDVSSRS--RTNYGMNVRG-----RPLVVLVDGVRLN
FhuA     7 DTITVTAAP         73 TPGVSVGTRGASNTYDHLIIRGFAAEGQSQNNYLNGLKLQ
PupA    68 NTVTVTASA        150 TPGITMSQDG-GERFNIY-SRG--SAIN--IYQFDGVTTY
IrgA     7 ETFVVSANR         51 VPGVTVTGGG---DTTDISIRG--MGSNYTLILVDGKRQT
FoxA     2 DTIEVTAKA         66 TPGVFTGFSGGATRYDTVALRGFHG-GDVNNTFLDGLRLL
```

2

3

```
           : : : | :   . *  . | : :   . | : :                . : | : :       *
OmpL2  131 QRLDVYNVGLQADSDFGGVQVFS-NSIYTR        193 MTIAQGNVADEAGRR
TBP1   125 KAVEISK-GSNS-VEQGSGALAGSVAFQTK        646 ID-PEKSFNKEAGIV
BtuB   105 QRVEYIR-GPRS-AVYGSDAIGGVVNIITT        410 LD-PEKSKQWE-GAF
Cir    106 ERIEVVR-GPMS-SLYGSDALGGVVNIITK        422 LK-PETSESWELGLY
IutA   103 HHIEVIF-GA-T-SLYGGGSTGGLINIVTK        507 LE-GVKVDSYELGWR
FhuA   127 ERAEIMR-GPVS-VLYGKSSPGGLLNMVSK        513 FA-PSKGKQYEVGVK
PupA   202 DRIEIVR-GATG-LMTGAGDPSAVVNVIRK        572 LD-PEVGKNYELGWK
IrgA   110 ERIEVIR-GPMS-TLYGSDAIGGVINIITR        447 LQ-PETSINKELSLM
FoxA   121 ERIDVIK-GPSS-ALYGQSIPGGVVMTSK         485 LK-PMTSEQYEVGII
```

4

5

```
           : : :   . *  . |                . : : : | * . | . : *  .           *
OmpL2  301 ERLSITGFD         481 VTVRLQNIRKWVY        505 EQKILFSGGLYF
TBP1   705 QSARITGIN         838 LRAGVYNLLNHRY        880 GRNYTFSLEMKF
BtuB   457 GKARIKGVE         561 VRGKIANLFDKDY        583 GREYTLSGSYTF
Cir    499 NKARNQGVE         604 LRAGVLNLGDKDL        627 GRRYFMAVDYRF
IutA   555 DKRRIYGVE         656 LSFSIENLFDRDY        695 RGRFGLNYSVLF
FhuA   563 GEIRARGVE         676 VALHVNNLFDREY        703 ERQVATATFRF
PupA   628 DGAETKGVD         738 ATLNVNNIFDKKY        761 PRNATVTLRYDF
IrgA   510 DEAETYGAE         618 IKAAVYNLFDQEV        641 GRRYWLGLDIAF
FoxA   534 GKVNSQGLE         646 VQLNVNNIADKKY        673 ERSVQATVGYDF
```

CLONED LEPTOSPIRA OUTER MEMBRANE PROTEIN

This is a divisional of application Ser. No. 08/249,013, filed May 25, 1994, now issued as U.S. Pat. No. 5,643,754.

This invention was made with Government support by the Veteran's Administration Research Advisory Group and Grant Nos. Al-21352, Al-29733, and Al-12601 awarded by the National Institutes of Health. The Government has certain rights in the invention.

BACKGROUND OF THE INVENTION

1. Field of the Invention

This invention relates generally to an antigenic preparation and specifically to a *Leptospira* outer membrane protein (OmpL2) which is used to induce a protective immune response in animals. Such a protein can be used immunologically as a vaccine for leptospirosis caused by this organism. Alternatively, diagnosis of leptospirosis can be performed by detecting the presence of the protein, antibody to the protein, or polynucleotide which encodes the protein.

2. Description of Related Art

Leptospirosis is a widespread zoonotic disease caused by pathogenic strains of *Leptospira* which are capable of infecting most mammalian species. At present, there are six pathogenic species and three nonpathogenic species within the genus *Leptospira*. Infection occurs either through direct contact with an infected animal or indirect contact with contaminated soil or water. In livestock, the disease causes economic losses due to abortion, stillbirth, infertility, decreased milk production, and death.

Efforts to control leptospirosis have been hampered because virulent leptospires have the capacity for both long-term survival in the environment as well as persistent infection and shedding by wildlife and livestock. Currently available leptospiral vaccines produce short-term immunity and do not provide cross-protection against many of the 170 serovars of pathogenic *Leptospira* (Thiermann, et al., *J. Am.Vet.Med.Assoc.* 184:722, 1984). These vaccines consist of inactivated whole organisms or outer envelope preparations which produce seroreactivity as determined by microscopic agglutination of intact organisms. The nature of the protective immunogens in these vaccine preparations has not been conclusively elucidated, although several lines of evidence suggest that lipopolysaccharide-like substance (LLS) may confer a degree of protection.

The pathogenesis of leptospirosis is very similar to that of other spirochetal diseases, including syphilis (caused by *Treponema pallidum*) and Lyme borreliosis (caused by *Borrelia burgdoferi*). Both syphilis and Lyme borreliosis are characterized by widespread dissemination early in the course of disease, including invasion of the central nervous system. *Leptospira* share this ability with other pathogenic spirochetes such that meningitis is a common manifestation of leptospirosis. Another feature of spirochetal infections is the ability to persist chronically in the host, as manifested in cases of tertiary syphilis and chronic Lyme arthritis.

In attempting to identify leptospiral outer membrane proteins (OMPs), previous research was unsuccessful due to such problems as: 1) the techniques used to identify surface-exposed proteins probably involved damage to the fragile leptospiral outer membrane resulting in exposure of subsurface structures; 2) putative surface-exposed proteins that were identified included a 35–36 kD doublet corresponding to *Leptospira endoflagella* (Kelson, et al.,*J. Med. Microbiol.* 26:47,1988), which are subsurface structures in spirochetes; and 3) use of SDS which nonselectively solubilizes proteins irrespective of their native cellular location.

Nunes-Edwards, et al. (*Infect. Immun.* 48:492, 1985) introduced the use of radioimmunoprecipitation and cell fractionation schemes based on the use of SDS in an effort to identify leptospiral OMPs. The leptospires used in their radioimmunoprecipitation procedure were subjected to high speed centrifugation (20,000×g) prior to the addition of antibody. Such high centrifugal forces cause mechanical disruption of the leptospiral outer membrane. Niikura, et al. (*Zbl. Bakt. Hyg. A.* 266:453, 1987) immunoprecipitated SDS-solubilized extracts of virulent and avirulent strains of *L. interrogans* serovar copenhageni that had been labeled by lactoperoxidase-catalyzed surface radioiodination. Since both of these studies precipitated a 35–36 kD doublet consistent with leptospiral endoflagella, there was a concern as to whether the other proteins identified might also have a subsurface rather than a surface location.

Jost, et al. (*J. Med. Microbiol.* 27:143) characterized a monoclonal antibody with specificity for a 35 kD proteinase K sensitive antigen which was present in a leptospiral outer envelope preparation. However, to demonstrate binding of the monoclonal antibody by immunoelectron microscopy, the leptospiral outer membrane had to be disrupted. Doherty, et al. (*J. Med. Microbiol.* 28:143) cloned two leptospiral proteins represented in an SDS-generated outer membrane preparation of *L. interrogans,* but did not provide corroborating evidence that these proteins are either constituents of the outer membrane or are surface-exposed.

Unsuccessful research on the identification of *Leptospira* and *T. pallidum* OMPs has shown the importance of taking into account spirochetal outer membrane fragility and the lack of outer membrane selectivity of ionic detergents such as sodium dodecyl sulfate (SDS) (Cunningham, et al, *J.Bacteriol.* 170:5789, 1988; Penn, et al., *J. Gen. Microbiol.* 131:2349, 1985; Stamm, et al., *Infect. Immun.* 55:2255, 1987). Outer membrane proteins are of great importance because they play a key role in bacterial pathogenesis. The identification of outer membrane proteins involved in *Leptospira* pathogenesis is significant to understanding not only leptospiral outer membrane proteins and their involvement in pathogenesis, but also to understanding other spirochetal outer membrane proteins and their role in pathogenesis.

SUMMARY OF THE INVENTION

The present invention is based on the identification of OmpL2 as a leptospiral outer membrane protein which is associated with pathogenic strains of *Leptospira*. Due to spirochetal outer membrane fragility and the fact that outer membrane proteins are present in small amounts, there have been no definitive reports of membrane spanning spirochetal outer membrane proteins until the present invention. The invention describes a 63 kD outer membrane protein from *Leptospira* and the gene encoding the protein. The deduced amino acid sequence has a typical leader peptidase I cleavage site, implying export beyond the inner membrane. The 63 kD protein has been designated OmpL2 for outer membrane protein of *Leptospira*. This immunogenic polypeptide is useful for inducing an immune response to pathogenic *Leptospira* as well as providing a diagnostic target for leptospirosis.

BRIEF DESCRIPTION OF THE DRAWINGS

FIG. 1A shows nucleotides 1 to 785, FIG. 1B shows nucleotides 786 to 1505, and FIG. 1C shows nucleotides 1506 to 1991, of the DNA sequence of OmpL2 (SEQ ID NO:

1). The deduced amino acid sequence (SEQ ID NO:2) is also shown (SEQ ID NOS: 1 and 2).

FIG. 2 shows an amino acid comparison between OmpL2 and eight TonB-dependent outer membrane proteins for seven regions of homology (SEQ ID NOS 3 and 10) identified by Kadner, R.,(Molecular Microbiology, 4:2027, 1990).

Figure 3:
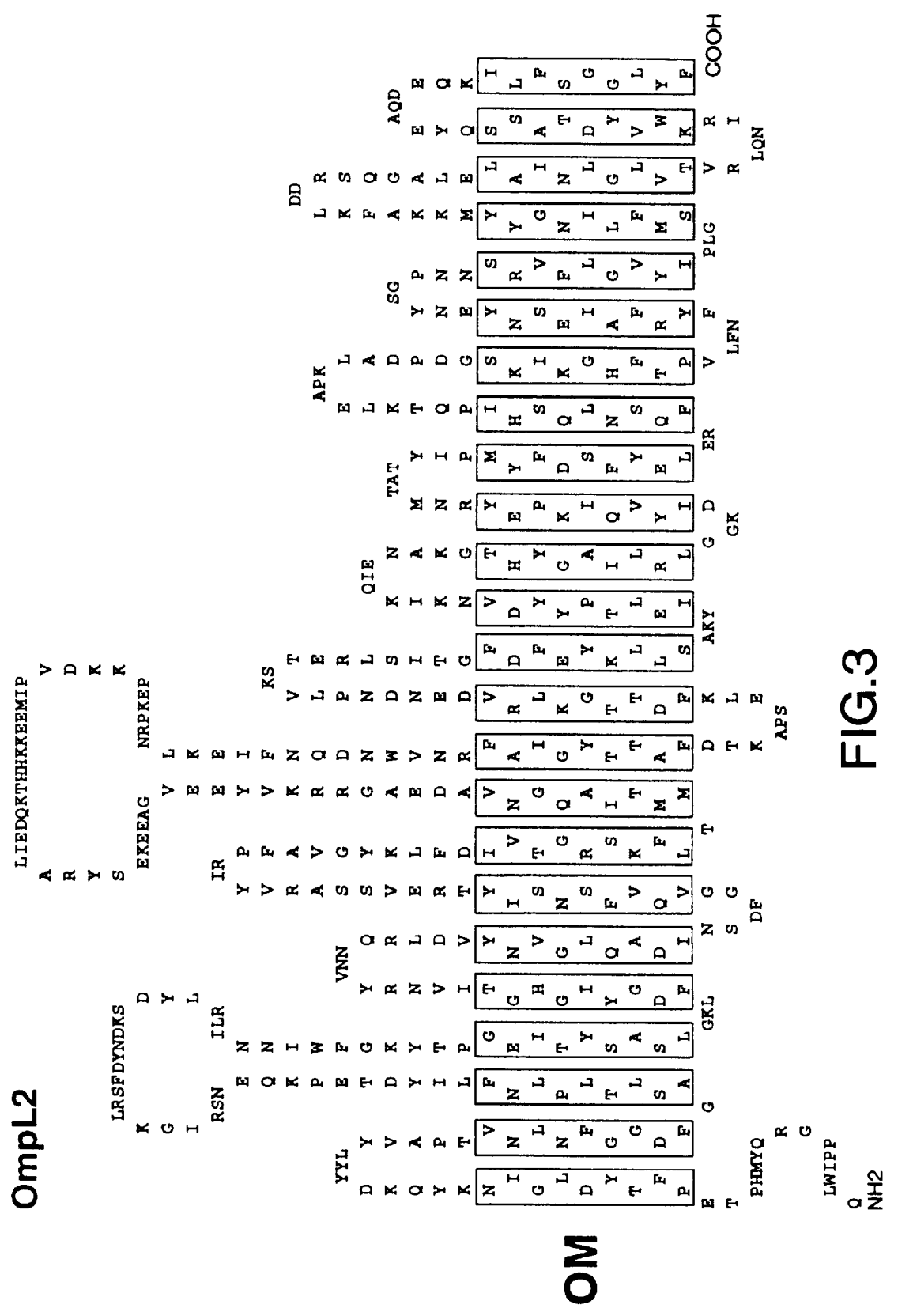

FIG. 3 shows a topological model of OmpL2. Membrane spanning beta-sheets are shown within rectangles in a staggered array with the hydrophobic, membrane-facing residues on the right side of the array.

DETAILED DESCRIPTION OF THE INVENTION

The present invention provides an isolated immunogenic polypeptide from an outer membrane protein of a pathogenic *Leptospira* species. Also included is a polynucleotide sequence which encodes the polypeptide. The outer membrane protein is a 63 kD protein originally isolated from *Leptospira alstoni* which has been termed OmpL2 and is a pathogen-associated exported protein of *Leptospira.* This immunogenic polypeptide is useful in a pharmaceutical composition for inducing an immune response to pathogenic *Leptospira.*

The invention includes a method of producing the polypeptide portion of an outer membrane protein of *Leptospira* using recombinant DNA techniques. The gene for the *L. alstoni* OmpL2 outer membrane protein is cloned into a plasmid vector which is then used to transform *E. coli.* When the OmpL2 gene is expressed in *E. coli,* the polypeptide produced has a molecular weight of approximately 63 kD as determined by SDS-polyacrylamide gel electrophoresis.

Recently, one approach to studying genes encoding exported leptospiral proteins was developed based on the concept underlying TnphoA transposition (Boquet, et al., *J. Bacteriol.* 169:1663, 1987; Hoffman, et al., *Proc. Natl. Acad. Sci. U.S.A.,* 82:5107, 1985; Manoil, et al., *Science* 233:1403, 1986; Manoil, et al., *J. Bacteriol.* 172:515, 1990). The system utilizes a phoA expression vector termed pMG, that contains an alkaline phosphatase (AP) gene lacking its signal sequence, together with the *E. coli* mutant strain KS330 (Strauch, et al., *Proc. Natl. Acad. Sci., U.S.A.* 85:1575, 1988), which possesses a leaky outer membrane, to identify genes encoding signal peptide export-dependent proteins which may function as virulence determinants. The screen for genes which encode exported proteins is done by identifying blue-halo colonies. The utility of this system has been confirmed for both *Treponema pallidum* (Blanco, et al., *Mol. Microbiol.* 5:2405, 1991) and *Leptospira alstoni* in which signal peptide containing proteins from both organisms were shown to be exported in *E. coli.* Such a method was utilized for identification of the ompL2 gene of the invention.

Sequence analysis showed that the OmpL2 structural gene consists of 1740 bases encoding a protein of 540 amino acids (SEQ ID NO:1 and 2). As expected for proteins to be exported beyond the inner membrane, the derived amino acid sequence begins with a 24-residue signal peptide. The OmpL2 sequence contains 24 stretches of amphipathic beta-sheet structure, consistent with outer membrane protein transmembrane segments, making it possible to propose a topological model with large surface-exposed loops and short periplasmic loops typical of outer membrane proteins.

Comparison of the OmpL2 sequence with that of known outer membrane proteins revealed areas of homology to the TonB-dependent outer membrane proteins. The TonB-dependent proteins form ligand-specific channels in the outer membrane of gram-negative bacteria. Seven stretches of sequence have been found to be conserved in all Ton B-dependent outer membrane proteins (Kadner, R. J., *Molecular Microbiology,* 4:2027–2033, 1990). Sequence comparison, using the GAP program (Devereux, J., et al., *Nucl. Acids Res.,* 12:387–395, 1984) demonstrated that the OmpL2 sequence is homologous in all seven of the conserved regions.

The bacterial genes for the OmpL2 outer membrane protein can likely be derived from any strain of pathogenic *Leptospira.* Preferably the protein is from *Leptospira alstoni,* strain RM52 (National Leptospirosis Reference Laboratory, Ames, Iowa). *Leptospira alstoni* is the most current name for the pathogenic *Leptospira* previously grouped together in the family of *Leptospira interrogans.* The *Leptospira interrogans* are publically available through the ATCC (Rockville, Md.), for example.

The invention provides polynucleotides encoding the *Leptospira* OmpL2 protein. These polynucleotides include DNA and RNA sequences which encode the protein. It is understood that all polynucleotides encoding all or a portion of OmpL2 are also included herein, so long as these polynucleotides exhibit the function of native or full length OmpL2, such as the ability to induce or bind antibody. Such polynucleotides include both naturally occurring and intentionally manipulated, for example, mutagenized polynucleotides.

DNA sequences of the invention can be obtained by several methods. For example, the DNA can be isolated using hybridization procedures which are well known in the art. These include, but are not limited to: 1) hybridization of probes to genomic libraries to detect shared nucleotide sequences and 2) antibody screening of expression libraries to detect shared structural features.

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. By using stringent hybridization conditions directed to avoid non-specific binding, it is possible, for example, to allow the autoradiographic visualization of a specific DNA clone by the hybridization of the target DNA to that single probe in the mixture which is its complete complement (Wallace, et al., *Nucleic Acid Research,* 9:879, 1981).

Alternatively, an expression library can be screened indirectly for OmpL2 peptides having at least one epitope using antibodies to OmpL2. Such antibodies can be either polyclonally or monoclonally derived and used to detect expression product indicative of the presence of OmpL2 DNA. Generally, a lambda gt11 library is constructed and screened immunologically according to the method of Huynh, et al., (in *DNA Cloning:A Practical Approach,* D. M. Glover, ed., 1:49,1985).

The development of specific DNA sequences encoding OmpL2 can also be obtained by: (1) isolation of a double-stranded DNA sequence from the genomic DNA, and (2) chemical manufacture of a DNA sequence to provide the necessary codons for the polypeptide of interest.

DNA sequences encoding OmpL2 can be expressed in vitro by DNA transfer into a suitable host cell. "Recombinant host cells" or "host cells" are cells in which a vector can be propagated and its DNA expressed. The term also includes any progeny of the subject host cell. It is understood that not all progeny are identical to the parental cell since there may be mutations that occur at replication. However, such progeny are included when the terms above are used.

The term "host cell" as used in the present invention is meant to include not only prokaryotes, but also, such eukaryotes as yeasts, filamentous fungi, as well as plant and animal cells. The term "prokaryote" is meant to include all bacteria which can be transformed with the gene for the expression of the OmpL2 outer membrane protein of *Leptospira*. Prokaryotic hosts may include Gram negative as well as Gram positive bacteria, such as *E. coli, S. typhimurium*, and *Bacillus subtilis.*

A recombinant DNA molecule coding for the OmpL2 protein can be used to transform a host using any of the techniques commonly known to those of ordinary skill in the art. Especially preferred is the use of a plasmid containing the OmpL2 coding sequence for purposes of prokaryotic transformation. Where the host is prokaryotic, such as *E. coli,* competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell.

In the present invention, the OmpL2 sequences may be inserted into a recombinant expression vector. The term "recombinant expression vector" refers to a plasmid, virus or other vehicle known in the art that has been manipulated by insertion or incorporation of OmpL2 genetic sequences. Such expression vectors contain a promotor sequence which facilitates the efficient transcription of the inserted genetic sequence in the host. The expression vector typically contains an origin of replication, a promoter, as well as specific genes which allow phenotypic selection of the transformed cells. The transformed prokaryotic hosts can be cultured according to means known in the art to achieve optimal cell growth. Various shuttle vectors for the expression of foreign genes in yeast have been reported (Heinemann, et al., *Nature,* 340:205, 1989; Rose, et al., *Gene,* 60:237, 1987). Biologically functional DNA vectors capable of expression and replication in a host are known in the art. Such vectors are used to incorporate DNA sequences of the invention.

Methods for preparing fused, operably linked genes and expressing them in bacteria are known and are shown, for example, in U.S. Pat. No. 4,366,246 which is incorporated herein by reference. The genetic constructs and methods described therein can be utilized for expression of *Leptospira* OmpL2 in prokaryotic hosts.

Examples of promoters which can be used in the invention are: rec A, trp, lac, tac, and bacteriophage lambda $p_R$ or $p_L$. Examples of plasmids which can be used in the invention are listed in Maniatis, et al.,(*Molecular Cloning,* Cold Spring Harbor Laboratories, 1982).

Antibodies provided in the present invention are immunoreactive with OmpL2 protein. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature,* 256:495, 1975; *Current Protocols in Molecular Biology,* Ausubel, et al., ed., 1989).

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual,* Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the OmpL2 polypeptide of the invention can be prepared using an intact polypeptide or fragments containing small peptides of interest as the immunizing antigen. The polypeptide or a peptide of SEQ ID NO:2 used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology,* Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Minor modifications of OmpL2 primary amino acid sequence may result in proteins which have substantially equivalent function compared to the OmpL2 protein described herein. Such modifications may be deliberate, as by site-directed mutagenesis, or may be spontaneous. All proteins produced by these modifications are included herein as long as OmpL2 function exists.

Modifications of OmpL2 primary amino acid sequence also include conservative variations. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Isolation and purification of microbially expressed protein, on fragments thereof, provided by the invention, may be carried out by conventional means including preparative chromatography and immunological separations involving monoclonal or polyclonal antibodies.

The invention extends to any host modified according to the methods described, or modified by any other methods, commonly known to those of ordinary skill in the art, such as, for example, by transfer of genetic material using a lysogenic phage, and which result in a prokaryote expressing the *Leptospira* gene for OmpL2 protein. Prokaryotes transformed with the *Leptospira* gene encoding the OmpL2 protein are particularly useful for the production of polypeptides which can be used for the immunization of an animal (e.g., a rabbit).

In one embodiment, the invention provides a pharmaceutical composition useful for inducing an immune response to pathogenic *Leptospira* in an animal comprising an immunologically effective amount of OmpL2 in a pharmaceutically acceptable carrier. The term "immunogenically effective amount," as used in describing the invention, is meant to denote that amount of *Leptospira* antigen which is necessary to induce in an animal the production of an immune response to *Leptospira*. The OmpL2 outer membrane protein of the invention is particularly useful in sensitizing the immune system of an animal such that, as one result, an immune response is produced which ameliorates the effect of *Leptospira* infection.

The OmpL2 outer membrane protein can be administered parenterally by injection, rapid infusion, nasopharyngeal absorption, dermal absorption, and orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable forms for suspending the liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, and sweetening, flavoring, and perfuming agents.

It is also possible for the antigenic preparations containing the OmpL2 protein of the invention to include an adjuvant. Adjuvants are substances that can be used to nonspecifically augment a specific immune response. Normally, the adjuvant and the antigen are mixed prior to presentation to the immune system, or presented separately, but into the same site of the animal being immunized. Adjuvants can be loosely divided into several groups based on their composition. These groups include oil adjuvants (for example, Freund's Complete and Incomplete), mineral salts (for example, $AlK(SO_4)_2$, $AlNa(SO_4)_2$, $AlNH_4(SO_4)$, silica, alum, $Al(OH)_3$, $Ca_3(PO_4)_2$, kaolin, and carbon), polynucleotides (for example, poly IC and poly AU acids), and certain natural substances (for example, wax D from *Mycobacterium tuberculosis*, as well as substances found in *Corynebacterium parvum*, *Bordetella pertussis*, and members of the genus *Brucella*).

In another embodiment, a method of inducing an immune response to pathogenic *Leptospira* in animal is provided. Many different techniques exist for the timing of the immunizations when a multiple immunization regimen is utilized. It is possible to use the antigenic preparation of the invention more than once to increase the levels and diversity of expression of the immune response of the immunized animal. Typically, if multiple immunizations are given, they will be spaced two to four weeks apart. Subjects in which an immune response to *Leptospira* is desirable include swine, cattle and humans.

Generally, the dosage of OmpL2 protein administered to an animal will vary depending on such factors as age, condition, sex and extent of disease, if any, and other variables which can be adjusted by one of ordinary skill in the art.

The antigenic preparations of the invention can be administered as either single or multiple dosages and can vary from about 10 ug to about 1,000 ug for the *Leptospira* OmpL2 antigen per dose, more preferably from about 50 ug to about 700 ug OmpL2 antigen per dose, most preferably from about 50 ug to about 300 ug OmpL2 antigen per dose.

When used for immunotherapy, the monoclonal antibodies of the invention may be unlabeled or labeled with a therapeutic agent. These agents can be coupled either directly or indirectly to the monoclonal antibodies of the invention. One example of indirect coupling is by use of a spacer moiety. These spacer moieties, in turn, can be either insoluble or soluble (Diener, et al., *Science*, 231:148, 1986) and can be selected to enable drug release from the monoclonal antibody molecule at the target site. Examples of therapeutic agents which can be coupled to the monoclonal antibodies of the invention for immunotherapy are drugs, radioisotopes, lectins, and toxins.

The labeled or unlabeled monoclonal antibodies of the invention can also be used in combination with therapeutic agents such as those described above. Especially preferred are therapeutic combinations comprising the monoclonal antibody of the invention and immunomodulators and other biological response modifiers.

When the monoclonal antibody of the invention is used in combination with various therapeutic agents, such as those described herein, the administration of the monoclonal antibody and the therapeutic agent usually occurs substantially contemporaneously. The term "substantially contemporaneously" means that the monoclonal antibody and the therapeutic agent are administered reasonably close together with respect to time. Usually, it is preferred to administer the therapeutic agent before the monoclonal antibody. For example, the therapeutic agent can be administered 1 to 6 days before the monoclonal antibody. The administration of the therapeutic agent can be daily, or at any other interval, depending upon such factors, for example, as the nature of the disorder, the condition of the patient and half-life of the agent.

The dosage ranges for the administration of monoclonal antibodies of the invention are those large enough to produce the desired effect in which the onset symptoms of the leptospiral disease are ameliorated. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg, in one or more dose administrations daily, for one or several days. Generally, when the monoclonal antibodies of the invention are administered conjugated with therapeutic agents, lower dosages, comparable to those used for in vivo diagnostic imaging, can be used.

The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

In a further embodiment, the invention provides a method of detecting a pathogenic *Leptospira*-associated disorder in a subject comprising contacting a cell component with a reagent which binds to the cell component. The cell component can be nucleic acid, such as DNA or RNA, or it can be protein. When the component is nucleic acid, the reagent is a nucleic acid probe or PCR primer. When the cell component is protein, the reagent is an antibody probe. The probes are detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

For purposes of the invention, an antibody or nucleic acid probe specific for OmpL2 may be used to detect the presence of OmpL2 polypeptide (using antibody) or polynucleotide (using nucleic acid probe) in biological fluids or tissues. Any specimen containing a detectable amount of OmpL2 antigen or polynucleotide can be used. A preferred specimen of this invention is blood, urine, cerebrospinal fluid, or tissue of endothelial origin.

When the cell component is nucleic acid, it may be necessary to amplify the nucleic acid prior to binding with a *Leptospira* specific probe. Preferably, polymerase chain reaction (PCR) is used, however, other nucleic acid amplification procedures such as ligase chain reaction (LCR), ligated activated transcription (LAT) and nucleic acid sequence-based amplification (NASBA) may be used.

Another technique which may also result in greater sensitivity consists of coupling antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific antihapten antibodies.

Alternatively, OmpL2 polypeptide can be used to detect antibodies to OmpL2 polypeptide in a specimen. The OmpL2 of the invention is particularly suited for use in immunoassays in which it can be utilized in liquid phase or bound to a solid phase carrier. In addition, OmpL2 used in these assays can be detectably labeled in various ways.

Examples of immunoassays which can utilize the OmpL2 of the invention are competitive and noncompetitive immunoassays in either a direct or indirect format. Examples of such immunoassays are the radioimmunoassay (RIA), the sandwich (immunometric assay) and the Western blot assay. Detection of antibodies which bind to the OmpL2 of the invention can be done utilizing immunoassays which run in either the forward, reverse, or simultaneous modes, including immunohistochemical assays on physiological samples. The concentration of OmpL2 which is used will vary depending on the type of immunoassay and nature of the detectable label which is used. However, regardless of the type of immunoassay which is used, the concentration of OmpL2 utilized can be readily determined by one of ordinary skill in the art using routine experimentation.

The OmpL2 of the invention can be bound to many different carriers and used to detect the presence of antibody specifically reactive with the polypeptide. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding OmpL2 or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

For purposes of the invention, the antibody which binds to OmpL2 of the invention may be present in various biological fluids and tissues. Any sample containing a detectable amount of antibodies to OmpL2 can be used. Normally, a sample is a liquid such as urine, saliva, cerebrospinal fluid, blood, serum and the like, or a solid or semi-solid such as tissue, feces and the like. The monoclonal antibodies of the invention, directed toward OmpL2, are also useful for the in vivo detection of antigen. The detectably labeled monoclonal antibody is given in a dose which is diagnostically effective. The term "diagnostically effective" means that the amount of detectably labeled monoclonal antibody is administered in sufficient quantity to enable detection of *Leptospira* OmpL2 antigen for which the monoclonal antibodies are specific.

The concentration of detectably labeled monoclonal antibody which is administered should be sufficient such that the binding to those cells, body fluid, or tissue having OmpL2 is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the subject. The dosage of monoclonal antibody can vary from about 0.001 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 key range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used to monitor the course of amelioration of *Leptospira* associated disorder. Thus, by measuring the increase or decrease of *Leptospira* OmpL2 polypeptide or antibodies to OmpL2 polypeptide present in various body fluids or tissues, it would be possible to determine whether a particular therapeutic regiment aimed at ameliorating the disorder is effective.

The materials for use in the method of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a OmpL2 binding reagent, such as an antibody. A second container may further comprise OmpL2 polypeptide. The constituents may be present in liquid or lyophilized form, as desired.

The following examples are intended to illustrate but not limit the invention. While they are typical of those that might be used, other procedures known to those skilled in the art may alternatively be used.

EXAMPLES

The following examples describe the identification of OmpL2 as an important leptospiral outer membrane protein. The method by which the ompL2 gene was cloned and sequenced is described. Sequence analysis and homology studies are shown, further indicating that OmpL2 is an outer membrane protein of pathogenic *Leptospira* and therefore is an excellent vaccine candidate.

EXAMPLE 1

Cloning of ompL2

The ompL2 gene was identified using an approach for identification of genes encoding exported leptospiral proteins by screening for blue-halo colonies using the pMG expresssion vector and *E. coli* KS330 (Blanco, et al., *Molecular Microbiology*, 5:2405, 1991; Giladi, et al., *J. Bacteriol.*, 175:4129, 1993). The pMG vector is a phoA expression vector, which, like TnphoA, is useful in identifying genes encoding membrane-spanning sequences or signal peptides. This cloning system has been modified to facilitate the distinction of outer membrane and periplasmic alkaline phosphatase (AP) fusion proteins from inner membrane AP fusion proteins by transforming pMG recombinants into *E. coli* KS330, the strain first used in the "blue halo" assay described by Strauch and Beckwith (*Proc. Natl. Acad. Sci., U.S.A.* 85:1576, 1988). The lipoprotein mutation lpp-5508 of KS330 results in an outer membrane that is leaky to macromolecules, and its degP4 mutation greatly reduces periplasmic proteolytic degradation of AP fusion proteins. pMG AP fusions containing cleavable signal peptides, including the *E. coli* periplasmic protein β-lactamase, OmpA and MOMP and Tp9, a *Treponema palladum* AP recombinant, have been shown to diffuse through the leaky outer membrane protein of KS330 and result in blue colonies with blue halos (Giladi, et al., supra). In contrast, inner membrane AP fusions derived from *E.coli* proteins, including leader peptidase, SecY, and the tetracycline resistance gene product, resulted in blue colonies without blue halos. The pMG/KS330r- cloning and screening approach identifies genes encoding proteins with cleavable signal peptides and therefore is useful in the identification of genes encoding potential virulence factors.

*Escherichia coli* strains were grown at 37° C. on Luria-Bertani medium. All restriction endonucleases and DNA-modifying enzymes were used in accordance with the specifications of the manufacturer (Bethesda Research Laboratories, Inc., Gaithersburg, Md., or Boehringer Mannheim Biochemicals, Indianapolis, Ind.).

*L. alstoni* strain RM52 (National Leptospirosis Reference Laboratory, Ames, Iowa) genomic DNA was prepared by the method of Yelton, D. B., and N. W. Charon, (*Gene*, 28:147, 1984). Genomic DNA was partially digested with Sau3A to a mean size of about 3.0 kb, ligated to BamHI-digested pMG and transformed into KS330r-. Approximately, 80,000 recombinant clones were screened on XP-IPTG-containing plates (Giladi, et al., supra), and about 10,000 clones were screened on XP plates without IPTG, yielding 226 blue colonies. Clones producing blue colonies were subcultured and spotted on high IPTG, high XP plates resulting in blue colonies, 66 of which showed blue halo formation. One such clone showing a blue halo, designated L2.086, was chosen for further study. This clone contained a 237 bp insert in pMG. The clone was identified as an outer membrane protein since it contained a leader sequence and leader peptidase I cleavage site (as determined from nucleic and deduced amino acid sequence) as indicated in FIG. 1(↑).

The remainder of the ompL2 gene was cloned on 3.0 kb EcoRI fragment. A library of the DNA from *L. alstoni* was generated in the λ Zap II vector system (Stratagene, San Diego, Calif.). Following digestion with EcoRI, the DNA fragments were ligated into the phage vector. The library was packaged and plated according to the manufacturer's recommendations. Approximately 10,000 plaques were plated, transferred to filters in duplicate, and processed as previously described (Maniatis, et al., *Molecular Cloning: A Laboratory Manual,* Cold Spring Harbor, N.Y., 1982). An oligonucleotide probe based on the L2.086 insert was radiolabled as described (Maniatis, et al., supra) and used for plaque hybridizations. Positive recombinant pBluescript SK(−) clones were recovered by in vivo excision according to the manufacturer's instructions.

EXAMPLE 2

Sequence Analysis for OmpL2

The L2.086 insert was sequenced in pMG by using the dideoxynucleotide chain termination method described by Sanger, et al., (*Proc. Natl. Acad. Sci. U.S.A.,* 74:5463, 1977) and [$\alpha$-$^{35}$S]-dATP (See Giladi, et al., supra). The remainder of the ompL2 gene was sequenced using standard M13 primers and custom oligonucleotide primers synthesized at UCLA, Dept. of Microbiology & Immunology for sequencing double-stranded templates. Sequencing reactions were performed for both strands using the Deaza T7 Sequencing kit protocol as described by Pharmacia Biotech, Inc., and [$\alpha$-$^{35}$S]dATP (specific activity, 1,000 Ci/mmol). DNA and deduced amino acid sequences were analyzed using DNA Strider 1.0 (Marck, C., *Nucl. Acids Res.* 16:1829, 1988). Protein homology searches were performed with the Profilesearch and FASTA programs found in the University of Wisconsin Genetics Computer Group (GCG), Inc., package, ver. 7.0 (Devereux, et al., *Nucl. Acids Res.* 12:387, 1984).

An open reading frame of 1740 bp was identified, which would encode a 540-amino-acid polypeptide with a predicted molecular mass of 63-kDa (FIG. 1). A Shine-Dalgarno ribosome binding site (RBS) was identified upstream from the ATG start codon, as well as putative −35 and −10 promoter regions. The TAA stop codon is indicated by an asterisk. Data base searching using the FASTA and ProfileSearch programs failed to reveal significant amino acid homologies. However, secondary structure analysis predicted numerous areas of amphipathic beta-sheets, consistent with outer membrane protein transmembrane segments. Of special note is the carboxy-terminal phenylalanine, a feature which is highly conserved among outer membrane proteins (Struyve, M., et al., *J. Mol. Biol,* 218:141–148, 1991).

Comparison of the OmpL2 sequence with that of known outer membrane proteins revealed areas of homology to the TonB-dependent outer membrane proteins. The TonB-dependent proteins form ligand-specific channels in the outer membrane of gram-negative bacteria. Seven stretches of sequence have been found to be conserved in all Ton B-dependent outer membrane proteins (Kadner, R. J., *Molecular Microbiology,* 4:2027–2033, 1990). Sequence comparison, using the GAP program (Devereux, J., et al., *Nucl. Acids Res.,* 12:387–395, 1984) demonstrated that the OmpL2 sequence is homologous in all seven of the conserved regions (FIG. 2). Peptide alignment between OmpL2 and eight TonB-dependent outer membrane proteins, for all seven regions of homology identified by Kadner, supra. Domain 1 is the "TonB box" which has been implicated in the direct interaction of Ton B with outer membrane receptors. OmpL2 is aligned with TBP1 (*N. gonorrhoeae* transferrin-binding protein 1); BtuB (*E. coli* vitamin B$_{12}$ receptor); Cir (*E. coli* colicin I receptor); Iuta (*E. coli* aerobactin receptor); FhuA (*E. coli* ferrichrome receptor); PupA (*P. putida* pseudobactin receptor); IrgA (*V. cholerae* iron-regulated outer membrane protein); FoxA (*Y. enterocolitica* ferrioxamine receptor). Asterisks mark positions of complete identity in all nine proteins. Positions are indicated where OmpL2 has a functionally similar amino acid as all (|), half (:), or 25% (.) of the other eight proteins, as predicted by the Mutation Matrix of Dayhoff. (In M. O. Dayhoff (ed.), Atlas of protein sequence and Structure, Vol. 5, Suppl. 3, National Biomedical Research Fdn., Washington, D.C.).

The first of these segments is known as the TonB box, which is characterized by the following consensus sequence: Thr-X-Y-Val. The OmpL2 TonB box retains the Threonine, but there is a conservative substitution of Isoleucine for Valine. A substitution at this position is unprecedented among the known TonB-dependent outer membrane proteins, however, spirochetes occupy one of the deepest branches in eubacterial evolution and OmpL2 would be the first spirochetal TonB-dependent outer membrane protein to be identified. Mutagenesis studies demonstrate that interaction of TonB-dependent outer membrane proteins with TonB are highly tolerant of amino acid substitutions within the TonB box, even at the invariant Valine positions (Gudmundsdottir, A., et al., *Journal of Bacteriology,* 171:6526–6533, 1989).

EXAMPLE 3

Topology of OmpL2

The topology of the *E. coli* TonB-dependent outer membrane protein, FepA, has been studied using monoclonal antibodies and deletion mutagenesis (Rutz, J. M., et al., *Science,* 258:471–474, 1992). A topology for the *Y. enterocolica* TonB-dependent outer membrane protein, FoxA, has also been proposed (Baumler, A. J., et al., *Molecular Microbiology,* 6:1309–1321, 1992). The OmpL2 sequence contains 24 stretches of amphipathic beta-sheets, consistent with transmembrane segments, making it possible to propose a topological model with large surface-exposed loops and short periplasmic loops typical of outer membrane proteins (FIG. 3). The membrane-spanning beta-sheets are shown within rectangles in a staggered array with the hydrophobic, membrane-facing residues on the right side of the array.

EXAMPLE 4

Expression of ompL2 during Iron Depletion

Studies show that OmpL2 is produced in greater amounts by *L. alstoni* when grown in iron-depleted media (bovuminar (Invirogen, N.Y.) containing 50 μM dipyridyl, an iron chelator). There is a potential Fur-binding site in the promoter region upstream of the ompL2 gene, which would also indicate that expression of ompL2 is turned on in iron-limiting conditions. This suggests that expression of OmpL2 occurs when *Leptospira* are in the host, a feature common to most of the Ton-B dependent outer membrane proteins. An outer membrane protein which is produced by a bacterial pathogen when it enters the host would be an ideal vaccine candidate.

EXAMPLE 5

Southern and Northern Blot Analysis

Southern blot analysis is performed as described previously by Maniatis, et al., supra. A probe from ompL2 is labeled at its 5' end with [$\gamma$-$^{32}$P]ATP (5,000 Ci/mmol; Amersham Corp., Arlington Heights, Ill.) and T4 polynucleotide kinase followed by purification over a BioSpin 6 column (Bio-rad Laboratories, Hercules, Calif.). Membranes containing DNA from various *Leptospira* species are hybridized overnight at 37° C. with 1×10$^6$ cpm/ml of hybridization buffer.

For Northern blot analysis, total cellular RNA is isolated from *L. alstoni* by the method as previously described (Maniatis, et al., supra). Approximately 15 µg of RNA is electrophoresed in duplicate through a 1.5% agarose-formaldehyde gel and transferred to nitrocellulose. The filters are probed with PCR-generated DNA fragments of ompL2 gene radiolabeled with [$\alpha$-$^{32}$P]dATP using the Random Primers DNA Labeling System (BRL). Hybridizations are conducted as previously described (Maniatis, et al., supra).

EXAMPLE 6

Cloning of the ompL2 Gene into the pRCET Expression Vector

The pBluescript plasmid containing the ompL2 gene was digested with HincII and ClaI. The resulting DNA fragment encoding the carboxy-terminal half of the OmpL2 protein was isolated by agarose gel electrophoresis, and ligated into pRSET (Invitrogen, San Diego, Calif.) digested with PvuIII and Csp45I. The resulting construct, pRSET-ompL2, encodes a fusion protein containing a 41 amino acid His6 binding site at the amino terminus of OmpL2. The six histidines allow for pH-dependent affinity purification of the fusion protein on a nickel resin column to the exclusion of *E. coli* proteins. The pRSET fusion protein is under T7 promoter control. After transformation of pRSET-ompL2 into *E. coli* DH5$\alpha$, milligram quantities of the His6-OmpL2 fusion protein are produced in the presence of isopropyl-$\beta$-D-thiogalactoside (IPTG, Sigma).

EXAMPLE 7

Immunization of Rabbits with Purified OmpL2

The His6-OmpL2 fusion protein is separated from other insoluble materials by SDS-PAGE. The His6-OmpL2 band containing about 50 micrograms of protein is cut out of the acrylamide gel, dessicated, ground to powder, mixed with Freund's complete adjuvant and inoculated subcutaneously and intramuscularly into a New Zealand White male rabbit. Additional His6-OmpL2 fusion protein is solubilized in 6M guanidine and purified over the nickel resin column and dialyzed in 10 mM Tris, pH 8.0. The secondary immunization is given six weeks after the primary immunization using roughly 50 micrograms of purified His6-OmpL2 fusion protein in Freund's incomplete adjuvant. The rabbit is bled two weeks after the secondary immunization. The post-boost antiserum will react with the 63-kDa antigen on immunoblots of whole *L. alstoni* separated by SDS-PAGE. Immunoblots of *L. alstoni* fractioned with TX-114 reveal reactivity with the 63-kDa OmpL2 antigen in the whole organism and detergent phase, but not the aqueous phase or insoluble pellet.

EXAMPLE 8

Surface Localization with Immunoelectron Microscopy

Having obtained a highly specific immunological reagent for localization studies, preliminary immunoelectron microscopy experiments can be conducted. A 20 µl suspension of 10$^7$ *L. alstoni* is added to 0.5 ml of heat-inactivated anti-OmpL2 antiserum or preimmune serum from the same rabbit and incubated for one hour with mixing. The bacteria are fixed for 30 minutes by addition of 250 µl of 0.75% glutaraldehyde in 100 mM cacodylate buffer, pH 7.0. The bacteria are washed, applied to electron microscopy grids, and probed with protein G-colloidal gold (10 nm particles).

EXAMPLE 9

Expression of OmpL2 with the pTrc 99A Expression Vector

The His6 fusion protein is well suited for purification, but is not appropriate for immunoblotting studies because of the potential for background reactivity to the 41 additional amino acids containing the His6 binding site. Preimmune sera from one of the rabbits reacts with the His6-OmpL2 fusion protein, but not with native OmpL2. A Bgl II-Hind II fragment is isolated from the pRCET-ompL2 vector by gel electrophoresis and cloned into the pTrc99A expression vector (Pharmacia) which had been reading frame adjusted with a 10-mer Nco I linker. The pTtrc99A-ompL2 construct, transformed into *E. coli* DH5$\alpha$ expresses the entire mature OmpL2 protein, plus a start methionine and only five additional amino acids supplied by the vector. *E. coli* DH5$\alpha$ containing the original pTrc99A vector serves as a negative control. Bacterial proteins are separated by SDS-PAGE and transferred to nitrocellulose, and probed with antisera from rabbits immunized with a variety of pathogenic *Leptospira* strains (antisera supplied by Dr. Arnold Kaufmann, Centers for Disease Control, Atlanta). Reactivity to OmpL2 is likely demonstrated with antisera to *L. interrogans*, serovars icterohaemorrhagiae, pomona, and bratislava, *L. alstoni*, serovars grippotyphosa and Mozdok, *L. santarosai*, serovars bakeri and canalzonae, and *L. weilii*, serovar celledoni. OmpL2 is likely not only expressed, but also antigenically conserved among pathogenic *Leptospira*, a feature that would make it an excellent vaccine candidate.

The foregoing is meant to illustrate, but not to limit, the scope of the invention. Indeed, those of ordinary skill in the art can readily envision and produce further embodiments, based on the teachings herein, without undue experimentation.

SUMMARY OF SEQUENCES

SEQ ID NO:1 is the nucleotide sequence and deduced amino acid sequence of ompL2.
SEQ ID NO:2 is the deduced amino acid sequence of OmpL2.
SEQ ID NO:3 is the amino acid sequence of TBP1.
SEQ ID NO:4 is the amino acid sequence of BtuB.
SEQ ID NO:5 is the amino acid sequence of Cir.
SEQ ID NO:6 is the amino acid sequence of IutA.
SEQ ID NO:7 is the amino acid sequence of FhuA.
SEQ ID NO:8 is the amino acid sequence of PupA.
SEQ ID NO:9 is the amino acid sequence of IrgA.
SEQ ID NO:10 is the amino acid sequence of FoxA.

5,824,321

I claim:

1. An isolated OmpL2 polypeptide, wherein:
   a) the peptide is an outer membrane protein of *Leptospira*
   b) the peptide binds an antibody specific for SEQ ID NO:2.

2. The polypeptide of claim 1, wherein the polypeptide is characterized as having a molecular weight of about 63 kD as determined by SDS polyacrylamide gel electrophoresis.

3. The polypeptide of claim 1, comprising the amino acid sequence as set forth in SEQ ID NO:2, or conservative variants thereof.

4. The polypeptide of claim 1, wherein the OmpL2 is from *Leptospira kirschneri*.

5. The polypeptide of claim 4, wherein the OmpL2 is from a serovar of *Leptospira kirschneri*.

6. The polypeptide of claim 1, wherein the OmpL2 is from *Leptospira interrogans*.

7. The polypeptide of claim 6, wherein the OmpL2 is from a serovar of *Leptospira interrogans* selected from the group consisting of icterohaemorrhagiae, pomona and bratislava.

8. The polypeptide of claim 1, wherein the protein has a leader peptidase I cleavage site.

9. A pharmaceutical composition useful for inducing an immune response to pathogenic *Leptospira* in an animal comprising an immunogenically effective amount of an OmpL2 polypeptide in a pharmaceutically acceptable carrier, wherein:
   a) the peptide is an outer membrane protein of *Leptospira*; and
   b) the peptide binds an antibody specific for SEQ ID NO:2.

10. The pharmaceutical composition of claim 9, wherein the pharmaceutically acceptable carrier contains an adjuvant.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
    ( A ) LENGTH: 1991 base pairs
    ( B ) TYPE: nucleic acid
    ( C ) STRANDEDNESS: single
    ( D ) TOPOLOGY: linear ( i i ) MOLECULE TYPE: DNA (genomic)

( v i i ) IMMEDIATE SOURCE:
    ( B ) CLONE: OmpL2

( i x ) FEATURE:
    ( A ) NAME/KEY: CDS
    ( B ) LOCATION: 96..1715

( x i ) SEQUENCE DESCRIPTION: SEQ ID NO:1:

```
GATCTTCATT  TCTTTCCGAA  AATTAAGTAA  GACTTTATTT  GTAAGGAGAG  TGTAGCGGGA                 60

TTTTCTAAGG  AATTTTCGGT  TTAAATCAAT  CTGAC ATG ACC AAA CGT TCT AAA                     113
                                          Met Thr Lys Arg Ser Lys
                                           1               5

TAC CTT TTC CTA TTT TTA TTT CTT TTC TTT GGA ATC CAA ACT GGA ATT                       161
Tyr Leu Phe Leu Phe Leu Phe Leu Phe Phe Gly Ile Gln Thr Gly Ile
            10              15                      20

CAA GCA CAA CTT TGG ATT CCA CCG GGT AGA CAG TAT ATG CAT CCC ACA                       209
Gln Ala Gln Leu Trp Ile Pro Pro Gly Arg Gln Tyr Met His Pro Thr
        25              30                      35

GAG CCG TTT ACT TAT GAC CTT GGG ATC AAT AAA TAT CAG AAA GAT TAT                       257
Glu Pro Phe Thr Tyr Asp Leu Gly Ile Asn Lys Tyr Gln Lys Asp Tyr
    40                      45                  50

TAT CTC TAT GTG GCG CCT ACC GTC AAT TTG AAC TTC GGA GGC GAT TTC                       305
Tyr Leu Tyr Val Ala Pro Thr Val Asn Leu Asn Phe Gly Gly Asp Phe
55              60                      65                  70

GGA GCC TCT CTG ACT TTA CCT TTA AAT TTT TTG ATC TAC GAT ACG GAG                       353
Gly Ala Ser Leu Thr Leu Pro Leu Asn Phe Leu Ile Tyr Asp Thr Glu
                75              80                      85

CCG AAA CAA GAA AAT TCT AGG ATC GGA AAG CTT AGG TCT TTC GAT TAC                       401
Pro Lys Gln Glu Asn Ser Arg Ile Gly Lys Leu Arg Ser Phe Asp Tyr
            90                      95                 100

AAT GAC AAA AGC GAT TAT CTT AGA TTG ATC AAT AAT ATT TGG TTT GGC                       449
Asn Asp Lys Ser Asp Tyr Leu Arg Leu Ile Asn Asn Ile Trp Phe Gly
        105                     110                     115

CAG TAT GGA AAA TAC ACT CCC GGA GAA ATT ACA TAT TCT GCA TCT TTA                       497
Gln Tyr Gly Lys Tyr Thr Pro Gly Glu Ile Thr Tyr Ser Ala Ser Leu
    120                     125                     130

GGA AAA CTA TTC GAT GGT TAT ATA GGT CAC GGA ACG ATC GTA AAC CGG                       545
Gly Lys Leu Phe Asp Gly Tyr Ile Gly His Gly Thr Ile Val Asn Arg
135             140                     145                 150

TAC GTA AAC AAT CAA CGT TTG GAT GTG TAT AAC GTA GGT CTT CAA GCA                       593
Tyr Val Asn Asn Gln Arg Leu Asp Val Tyr Asn Val Gly Leu Gln Ala
                155                     160                     165

GAT ATA AAC AGT GAC TTT GGA GGA GTG CAG GTA TTT TCT AAT TCG ATC                       641
Asp Ile Asn Ser Asp Phe Gly Gly Val Gln Val Phe Ser Asn Ser Ile
            170                     175                     180

TAT ACG AGA GAA GTC AGT TCA GCA AGG GTT TAT ATC CGG CCC TTT GCC                       689
Tyr Thr Arg Glu Val Ser Ser Ala Arg Val Tyr Ile Arg Pro Phe Ala
        185                     190                     195
```

```
GTT GGA TAT AAA CTT TTT GAT ATT GTT ACC GGC CGG TCC AAA TTT TTG        737
Val Gly Tyr Lys Leu Phe Asp Ile Val Thr Gly Arg Ser Lys Phe Leu
        200                 205                 210

ACG ATG ATG ACA ATC GCA CAA GGA AAC GTA GCA GAC GAG GCT GGA AGA        785
Thr Met Met Thr Ile Ala Gln Gly Asn Val Ala Asp Glu Ala Gly Arg
215                 220                 225                 230

AGA AAA GTT TAT GAA GAA GTA GGG GCG GAA GAA AAG GAA TCT TAT CGC        833
Arg Lys Val Tyr Glu Glu Val Gly Ala Glu Glu Lys Glu Ser Tyr Arg
                235                 240                 245

GCT TTG ATC GAG GAT CAG AAG ACG CAC CAC AAA AAA GAA GAG ATG ATT        881
Ala Leu Ile Glu Asp Gln Lys Thr His His Lys Lys Glu Glu Met Ile
        250                 255                 260

CCT GTG GAT AAG AAA CCG GAA AAA CCT CGA AAT TTA AAA GAA ATA TTT        929
Pro Val Asp Lys Lys Pro Glu Lys Pro Arg Asn Leu Lys Glu Ile Phe
            265                 270                 275

AAT CAA GAT AAT TGG GTT AAC CGG TTT GCA ATT GGT TAT ACG ACT GCG        977
Asn Gln Asp Asn Trp Val Asn Arg Phe Ala Ile Gly Tyr Thr Thr Ala
280                 285                 290

TTT GAT ACC AAA GCC CCT TCG GAA CTT AAG TTT GAT ACG ACT GGA AAA       1025
Phe Asp Thr Lys Ala Pro Ser Glu Leu Lys Phe Asp Thr Thr Gly Lys
295                 300                 305                 310

TTG AGA GTG GAT GAA AAC GAC AAT CCA CTC GTC AAG TCT ACG GAA AGA       1073
Leu Arg Val Asp Glu Asn Asp Asn Pro Leu Val Lys Ser Thr Glu Arg
                315                 320                 325

CTT TCG ATC ACT GGT TTC GAT TTC GAA TAT AAA TTA CTC AGT GCG AAA       1121
Leu Ser Ile Thr Gly Phe Asp Phe Glu Tyr Lys Leu Leu Ser Ala Lys
        330                 335                 340

TAT ATA GAA CTG ACT CCC TAT TAC GAC GTA AAT AAA ATC AAA CAG ATA       1169
Tyr Ile Glu Leu Thr Pro Tyr Tyr Asp Val Asn Lys Ile Lys Gln Ile
            345                 350                 355

GAA AAC GCA AAA GGT ACA CAT TAC GGA GCG ATT CTT CGA TTG GGT GGA       1217
Glu Asn Ala Lys Gly Thr His Tyr Gly Ala Ile Leu Arg Leu Gly Gly
360                 365                 370

AAG GAC ATT TAT GTA CAA ATA AAA CCT GAA TAT AGA AAT ATG ACT GCA       1265
Lys Asp Ile Tyr Val Gln Ile Lys Pro Glu Tyr Arg Asn Met Thr Ala
375                 380                 385                 390

ACG TAT ATT CCT ATG TAT TTT GAT AGT TTT TAC GAA TTG GAA AGG TTT       1313
Thr Tyr Ile Pro Met Tyr Phe Asp Ser Phe Tyr Glu Leu Glu Arg Phe
                395                 400                 405

CAG AGT AAT TTA CAA AGT CAT ATT CCG CAG ACT AAA TTA GAA GCC CCA       1361
Gln Ser Asn Leu Gln Ser His Ile Pro Gln Thr Lys Leu Glu Ala Pro
        410                 415                 420

AAA TTA GCC GAT CCG GAT GGA TCT AAG ATA AAA GGA CAT TTT ACA CCT       1409
Lys Leu Ala Asp Pro Asp Gly Ser Lys Ile Lys Gly His Phe Thr Pro
            425                 430                 435

GTA TTA TTC AAC TTT TAT AGA TTT GCG ATT GAA TCG AAT TAC GAG AAT       1457
Val Leu Phe Asn Phe Tyr Arg Phe Ala Ile Glu Ser Asn Tyr Glu Asn
440                 445                 450

TAT TCC GGG CCG AAT AAC TCT AGA GTA TTT TTA GGA GTT TAT ATT CCG       1505
Tyr Ser Gly Pro Asn Asn Ser Arg Val Phe Leu Gly Val Tyr Ile Pro
455                 460                 465                 470

CTT GGA AGT ATG TTC CTA ATT AAT GGA TAT TAT ATG AAA AAA GCT TTT       1553
Leu Gly Ser Met Phe Leu Ile Asn Gly Tyr Tyr Met Lys Lys Ala Phe
                475                 480                 485

AAA TTA GAC GAT CGA TCT CAA GGG GCC TTA GAA TTG GCG ATC AAT TTG       1601
Lys Leu Asp Asp Arg Ser Gln Gly Ala Leu Glu Leu Ala Ile Asn Leu
        490                 495                 500

GGG CTT GTA ACA GTT AGG CTT CAG AAT ATA CGT AAA TGG GTT TAT GAT       1649
Gly Leu Val Thr Val Arg Leu Gln Asn Ile Arg Lys Trp Val Tyr Asp
            505                 510                 515
```

```
ACG  GCT  TCT  AGT  CAA  TAC  GAA  GCC  CAA  GAC  GAA  CAG  AAG  ATA  TTA  TTT              1697
Thr  Ala  Ser  Ser  Gln  Tyr  Glu  Ala  Gln  Asp  Glu  Gln  Lys  Ile  Leu  Phe
     520                      525                      530

TCC  GGT  GGT  TTA  TAT  TTT  TAAAAAAGTA  TTTTTCTTC  AAGTCTTGCG                              1745
Ser  Gly  Gly  Leu  Tyr  Phe
535                      540

AGTAAAAATG  CAAAAGCTGT  TTCTGTACGA  AGAACTCGAT  CGGAAAGATT  TAATTTTTG                         1805

AAACCGAAAC  GTTTCCAAAA  ATCGATTTCG  TTTGGAACAA  ATCCACTTTC  CGGACCGATC                         1865

GCGGATAAAA  TACGAGGTAT  TTAGAATAC   ATTCCAAAAT  TTGAATCTAA  TTTTTTTCT                          1925

TTAAACATCT  GGGTAAAAGT  AAAACCTTTT  CGATCTAAAA  CAAAACGAAA  CGTAAAGTCT                         1985

AATTCT                                                                                        1991
```

( 2 ) INFORMATION FOR SEQ ID NO:2:

( i ) SEQUENCE CHARACTERISTICS:
        ( A ) LENGTH: 540 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Thr  Lys  Arg  Ser  Lys  Tyr  Leu  Phe  Leu  Phe  Leu  Phe  Leu  Phe  Phe
1                   5                        10                      15

Gly  Ile  Gln  Thr  Gly  Ile  Gln  Ala  Gln  Leu  Trp  Ile  Pro  Pro  Gly  Arg
               20                       25                           30

Gln  Tyr  Met  His  Pro  Thr  Glu  Pro  Phe  Thr  Tyr  Asp  Leu  Gly  Ile  Asn
               35                       40                      45

Lys  Tyr  Gln  Lys  Asp  Tyr  Tyr  Leu  Tyr  Val  Ala  Pro  Thr  Val  Asn  Leu
          50                       55                 60

Asn  Phe  Gly  Gly  Asp  Phe  Gly  Ala  Ser  Leu  Thr  Leu  Pro  Leu  Asn  Phe
65                       70                      75                           80

Leu  Ile  Tyr  Asp  Thr  Glu  Pro  Lys  Gln  Glu  Asn  Ser  Arg  Ile  Gly  Lys
                    85                       90                      95

Leu  Arg  Ser  Phe  Asp  Tyr  Asn  Asp  Lys  Ser  Asp  Tyr  Leu  Arg  Leu  Ile
               100                      105                     110

Asn  Asn  Ile  Trp  Phe  Gly  Gln  Tyr  Gly  Lys  Tyr  Thr  Pro  Gly  Glu  Ile
          115                      120                     125

Thr  Tyr  Ser  Ala  Ser  Leu  Gly  Lys  Leu  Phe  Asp  Gly  Tyr  Ile  Gly  His
     130                      135                     140

Gly  Thr  Ile  Val  Asn  Arg  Tyr  Val  Asn  Asn  Gln  Arg  Leu  Asp  Val  Tyr
145                      150                     155                          160

Asn  Val  Gly  Leu  Gln  Ala  Asp  Ile  Asn  Ser  Asp  Phe  Gly  Gly  Val  Gln
               165                      170                     175

Val  Phe  Ser  Asn  Ser  Ile  Tyr  Thr  Arg  Glu  Val  Ser  Ser  Ala  Arg  Val
               180                      185                     190

Tyr  Ile  Arg  Pro  Phe  Ala  Val  Gly  Tyr  Lys  Leu  Phe  Asp  Ile  Val  Thr
               195                      200                     205

Gly  Arg  Ser  Lys  Phe  Leu  Thr  Met  Met  Thr  Ile  Ala  Gln  Gly  Asn  Val
     210                      215                     220

Ala  Asp  Glu  Ala  Gly  Arg  Arg  Lys  Val  Tyr  Glu  Val  Gly  Ala  Glu
225                      230                     235                          240

Glu  Lys  Glu  Ser  Tyr  Arg  Ala  Leu  Ile  Glu  Asp  Gln  Lys  Thr  His  His
               245                      250                     255

Lys  Lys  Glu  Glu  Met  Ile  Pro  Val  Asp  Lys  Lys  Pro  Glu  Lys  Pro  Arg
```

|  |  |  |  |  | 260 |  |  |  |  | 265 |  |  |  |  | 270 |  |
|---|---|---|---|---|---|---|---|---|---|---|---|---|---|---|---|---|

Asn Leu Lys Glu Ile Phe Asn Gln Asp Asn Trp Val Asn Arg Phe Ala
        275                  280                285

Ile Gly Tyr Thr Thr Ala Phe Asp Thr Lys Ala Pro Ser Glu Leu Lys
   290                  295                300

Phe Asp Thr Thr Gly Lys Leu Arg Val Asp Glu Asn Asp Pro Leu
305                  310              315              320

Val Lys Ser Thr Glu Arg Leu Ser Ile Thr Gly Phe Asp Phe Glu Tyr
                  325              330              335

Lys Leu Leu Ser Ala Lys Tyr Ile Glu Leu Thr Pro Tyr Tyr Asp Val
        340              345              350

Asn Lys Ile Lys Gln Ile Glu Asn Ala Lys Gly Thr His Tyr Gly Ala
       355               360              365

Ile Leu Arg Leu Gly Gly Lys Asp Ile Tyr Val Gln Ile Lys Pro Glu
   370                  375              380

Tyr Arg Asn Met Thr Ala Thr Tyr Ile Pro Met Tyr Phe Asp Ser Phe
385                  390              395              400

Tyr Glu Leu Glu Arg Phe Gln Ser Asn Leu Gln Ser His Ile Pro Gln
                  405              410              415

Thr Lys Leu Glu Ala Pro Lys Leu Ala Asp Pro Asp Gly Ser Lys Ile
            420              425              430

Lys Gly His Phe Thr Pro Val Leu Phe Asn Phe Tyr Arg Phe Ala Ile
       435               440              445

Glu Ser Asn Tyr Glu Asn Tyr Ser Gly Pro Asn Asn Ser Arg Val Phe
     450               455              460

Leu Gly Val Tyr Ile Pro Leu Gly Ser Met Phe Leu Ile Asn Gly Tyr
465                  470              475              480

Tyr Met Lys Lys Ala Phe Lys Leu Asp Asp Arg Ser Gln Gly Ala Leu
            485              490              495

Glu Leu Ala Ile Asn Leu Gly Leu Val Thr Val Arg Leu Gln Asn Ile
        500              505              510

Arg Lys Trp Val Tyr Asp Thr Ala Ser Ser Gln Tyr Glu Ala Gln Asp
       515               520              525

Glu Gln Lys Ile Leu Phe Ser Gly Gly Leu Tyr Phe
530                  535              540

( 2 ) INFORMATION FOR SEQ ID NO:3:

( i ) SEQUENCE CHARACTERISTICS:
        ( A ) LENGTH: 122 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: TBP1

( i x ) FEATURE:
        ( A ) NAME/KEY: Protein
        ( B ) LOCATION: 1..122

( x i ) SEQUENCE DESCRIPTION: SEQ ID NO:3:

Asp Thr Ile Gln Val Lys Ala Lys Lys Asp Pro Gly Ile Ala Val Val
1                5                  10              15

Glu Gln Gly Arg Gly Ala Ser Ser Gly Tyr Ser Ile Arg Gly Met Asp
            20              25              30

Lys Asn Arg Val Ser Leu Thr Val Asp Gly Leu Ala Gln Ile Lys Ala

```
                        35                           40                            45
        Val  Glu  Ile  Ser  Lys  Gly  Ser  Asn  Ser  Val  Glu  Gln  Gly  Ser  Gly  Ala
              50                           55                           60

Leu  Ala  Gly  Ser  Val  Ala  Phe  Gln  Thr  Lys  Ile  Asp  Pro  Glu  Lys  Ser
        65                      70                           75                      80

Phe  Asn  Lys  Glu  Ala  Gly  Ile  Val  Gln  Ser  Ala  Arg  Ile  Thr  Gly  Ile
                             85                           90                      95

Asn  Leu  Arg  Ala  Gly  Val  Tyr  Asn  Leu  Leu  Asn  His  Arg  Tyr  Gly  Arg
                        100                      105                      110

Asn  Tyr  Thr  Phe  Ser  Leu  Glu  Met  Lys  Phe
                        115                      120
```

( 2 ) INFORMATION FOR SEQ ID NO:4:

( i ) SEQUENCE CHARACTERISTICS:
        ( A ) LENGTH: 122 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: BtuB ( i x ) FEATURE:
        ( A ) NAME/KEY: Protein
        ( B ) LOCATION: 1..122

( x i ) SEQUENCE DESCRIPTION: SEQ ID NO:4:

```
        Asp  Thr  Leu  Val  Val  Thr  Ala  Asn  Arg  Leu  Pro  Gly  Val  Asp  Ile  Thr
        1                       5                            10                      15

Gln  Asn  Gly  Gly  Ser  Gly  Gln  Leu  Ser  Ser  Ile  Phe  Ile  Arg  Gly  Thr
                        20                           25                      30

Asn  Ala  Ser  His  Val  Leu  Val  Leu  Ile  Asp  Gly  Val  Arg  Leu  Asn  Gln
                        35                           40                      45

Arg  Val  Glu  Tyr  Ile  Arg  Gly  Pro  Arg  Ser  Ala  Val  Tyr  Gly  Ser  Asp
              50                           55                           60

Ala  Ile  Gly  Gly  Val  Val  Asn  Ile  Ile  Thr  Thr  Leu  Asp  Pro  Glu  Lys
        65                      70                           75                      80

Ser  Lys  Gln  Trp  Glu  Gly  Ala  Phe  Gly  Lys  Ala  Arg  Ile  Lys  Gly  Val
                        85                           90                      95

Glu  Val  Arg  Gly  Lys  Ile  Ala  Asn  Leu  Phe  Asp  Lys  Asp  Tyr  Gly  Arg
                        100                      105                      110

Glu  Tyr  Thr  Leu  Ser  Gly  Ser  Tyr  Thr  Phe
                        115                      120
```

( 2 ) INFORMATION FOR SEQ ID NO:5:

( i ) SEQUENCE CHARACTERISTICS:
        ( A ) LENGTH: 121 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: Cir ( i x ) FEATURE:
        ( A ) NAME/KEY: Protein
        ( B ) LOCATION: 1..121

( x i ) SEQUENCE DESCRIPTION: SEQ ID NO:5:

Glu Thr Met Val Val Thr Ala Ser Ser Val Pro Gly Val Gln Leu Thr
1               5                       10                      15

Asn Glu Gly Asp Asn Arg Lys Gly Val Ser Ile Arg Gly Leu Asp Ser
            20              25              30

Ser Tyr Thr Leu Ile Leu Val Asp Gly Lys Arg Val Asn Glu Arg Ile
        35              40              45

Glu Val Val Arg Gly Pro Met Ser Ser Leu Tyr Gly Ser Asp Ala Leu
    50              55              60

Gly Gly Val Val Asn Ile Ile Thr Lys Leu Lys Pro Glu Thr Ser Glu
65              70              75                      80

Ser Trp Glu Leu Gly Leu Tyr Asn Lys Ala Arg Asn Gln Gly Val Glu
            85              90                      95

Leu Arg Ala Gly Val Leu Asn Leu Gly Asp Lys Asp Leu Gly Arg Arg
            100             105             110

Tyr Phe Met Ala Val Asp Tyr Arg Phe
        115             120

(2) INFORMATION FOR SEQ ID NO:6:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: IutA (ix) FEATURE:
        (A) NAME/KEY: Protein
        (B) LOCATION: 1..117

(xi) SEQUENCE DESCRIPTION: SEQ ID NO:6:

Glu Thr Phe Val Val Ser Ala Asn Arg Ile Pro Gly Leu Asp Val Ser
1               5                       10                      15

Ser Arg Ser Arg Thr Asn Tyr Gly Met Asn Val Arg Gly Arg Pro Leu
            20              25              30

Val Val Leu Val Asp Gly Val Arg Leu Asn His His Ile Glu Val Ile
        35              40              45

Phe Gly Ala Thr Ser Leu Tyr Gly Gly Gly Ser Thr Gly Gly Leu Ile
    50              55              60

Asn Ile Val Thr Lys Leu Glu Gly Val Lys Val Asp Ser Tyr Glu Leu
65              70              75                      80

Gly Trp Arg Asp Lys Arg Arg Ile Tyr Gly Val Glu Leu Ser Phe Ser
            85              90                      95

Ile Glu Asn Leu Phe Asp Arg Asp Tyr Arg Gly Arg Phe Gly Leu Asn
            100             105             110

Tyr Ser Val Leu Phe
        115

(2) INFORMATION FOR SEQ ID NO:7:

(i) SEQUENCE CHARACTERISTICS:
        (A) LENGTH: 125 amino acids
        (B) TYPE: amino acid
        (C) STRANDEDNESS: single
        (D) TOPOLOGY: linear (ii) MOLECULE TYPE: protein ( v i i ) IMMEDIATE SOURCE:
    ( B ) CLONE: FhuA ( i x ) FEATURE:
    ( A ) NAME/KEY: Protein
    ( B ) LOCATION: 1..125

( x i ) SEQUENCE DESCRIPTION: SEQ ID NO:7:

```
Asp Thr Ile Thr Val Thr Ala Ala Pro Thr Pro Gly Val Ser Val Gly
1               5                   10                  15

Thr Arg Gly Ala Ser Asn Thr Tyr Asp His Leu Ile Ile Arg Gly Phe
            20                  25                  30

Ala Ala Glu Gly Gln Ser Gln Asn Asn Tyr Leu Asn Gly Leu Lys Leu
        35                  40                  45

Gln Glu Arg Ala Glu Ile Met Arg Gly Pro Val Ser Val Leu Tyr Gly
    50                  55                  60

Lys Ser Ser Pro Gly Gly Leu Leu Asn Met Val Ser Lys Phe Ala Pro
65                  70                  75                  80

Ser Lys Gly Lys Gln Tyr Glu Val Gly Val Lys Gly Glu Ile Arg Ala
                85                  90                  95

Arg Gly Val Glu Val Ala Leu His Val Asn Asn Leu Phe Asp Arg Glu
            100                 105                 110

Tyr Glu Arg Gln Val Val Ala Thr Ala Thr Phe Arg Phe
        115                 120                 125
```

( 2 ) INFORMATION FOR SEQ ID NO:8:

( i ) SEQUENCE CHARACTERISTICS:
        ( A ) LENGTH: 119 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: PupA ( i x ) FEATURE:
        ( A ) NAME/KEY: Protein
        ( B ) LOCATION: 1

( x i ) SEQUENCE DESCRIPTION: SEQ ID NO:8:

```
Asn Thr Val Thr Val Thr Ala Ser Ala Thr Pro Gly Ile Thr Met Ser
1               5                   10                  15

Gln Asp Gly Gly Glu Arg Phe Asn Ile Tyr Ser Arg Gly Ser Ala Ile
            20                  25                  30

Asn Ile Tyr Gln Phe Asp Gly Val Thr Thr Tyr Asp Arg Ile Glu Ile
        35                  40                  45

Val Arg Gly Ala Thr Gly Leu Met Thr Gly Ala Gly Asp Pro Ser Ala
    50                  55                  60

Val Val Asn Val Ile Arg Lys Leu Asp Pro Glu Val Gly Lys Asn Tyr
65                  70                  75                  80

Glu Leu Gly Trp Lys Asp Gly Ala Glu Thr Lys Gly Val Asp Ala Thr
                85                  90                  95

Leu Asn Val Asn Asn Ile Phe Asp Lys Lys Tyr Pro Arg Asn Ala Thr
            100                 105                 110

Val Thr Leu Arg Tyr Asp Phe
        115
```

( 2 ) INFORMATION FOR SEQ ID NO:9:

( i ) SEQUENCE CHARACTERISTICS:
    ( A ) LENGTH: 120 amino acids
    ( B ) TYPE: amino acid
    ( C ) STRANDEDNESS: single
    ( D ) TOPOLOGY: linear ( i i ) MOLECULE TYPE: protein ( v i i ) IMMEDIATE SOURCE:
    ( B ) CLONE: IrgA ( i x ) FEATURE:
    ( A ) NAME/KEY: Protein
    ( B ) LOCATION: 1..120

( x i ) SEQUENCE DESCRIPTION: SEQ ID NO:9:

```
Glu Thr Phe Val Val Ser Ala Asn Arg Val Pro Gly Val Thr Val Thr
1               5                   10                  15

Gly Gly Gly Asp Thr Thr Asp Ile Ser Ile Arg Gly Met Gly Ser Asn
            20                  25                  30

Tyr Thr Leu Ile Leu Val Asp Gly Lys Arg Gln Thr Glu Arg Ile Glu
            35                  40                  45

Val Ile Arg Gly Pro Met Ser Thr Leu Tyr Gly Ser Asp Ala Ile Gly
        50                  55                  60

Gly Val Ile Asn Ile Ile Thr Arg Leu Gln Pro Glu Thr Ser Ile Asn
65                  70                  75                  80

Lys Glu Leu Ser Leu Met Asp Glu Ala Glu Thr Tyr Gly Ala Glu Ile
                85                  90                  95

Lys Ala Ala Val Tyr Asn Leu Phe Asp Gln Glu Val Gly Arg Arg Tyr
            100                 105                 110

Trp Leu Gly Leu Asp Ile Ala Phe
            115             120
```

( 2 ) INFORMATION FOR SEQ ID NO:10:

( i ) SEQUENCE CHARACTERISTICS:
        ( A ) LENGTH: 124 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: FoxA ( i x ) FEATURE:
        ( A ) NAME/KEY: Protein
        ( B ) LOCATION: 1..124

( x i ) SEQUENCE DESCRIPTION: SEQ ID NO:10:

```
Asp Thr Ile Glu Val Thr Ala Lys Ala Thr Pro Gly Val Phe Thr Gly
1               5                   10                  15

Phe Ser Gly Gly Ala Thr Arg Tyr Asp Thr Val Ala Leu Arg Gly Phe
            20                  25                  30

His Gly Gly Asp Val Asn Asn Thr Phe Leu Asp Gly Leu Arg Leu Leu
            35                  40                  45

Glu Arg Ile Asp Val Ile Lys Gly Pro Ser Ser Ala Leu Tyr Gly Gln
        50                  55                  60

Ser Ile Pro Gly Gly Val Val Met Met Thr Ser Lys Leu Lys Pro Met
65                  70                  75                  80

Thr Ser Glu Gln Tyr Glu Val Gly Ile Ile Gly Lys Val Asn Ser Gln
                85                  90                  95

Gly Leu Glu Val Gln Leu Asn Val Asn Asn Ile Ala Asp Lys Lys Tyr
```

-continued

```
              100                        105                         110
Glu  Arg  Ser  Val  Gln  Ala  Thr  Val  Gly  Tyr  Asp  Phe
               115                        120
```